Nov. 6, 1962 E. B. LE GRICE Plant Pat. 2,189
ROSA FLORIBUNDA PLANT
Filed May 2, 1961
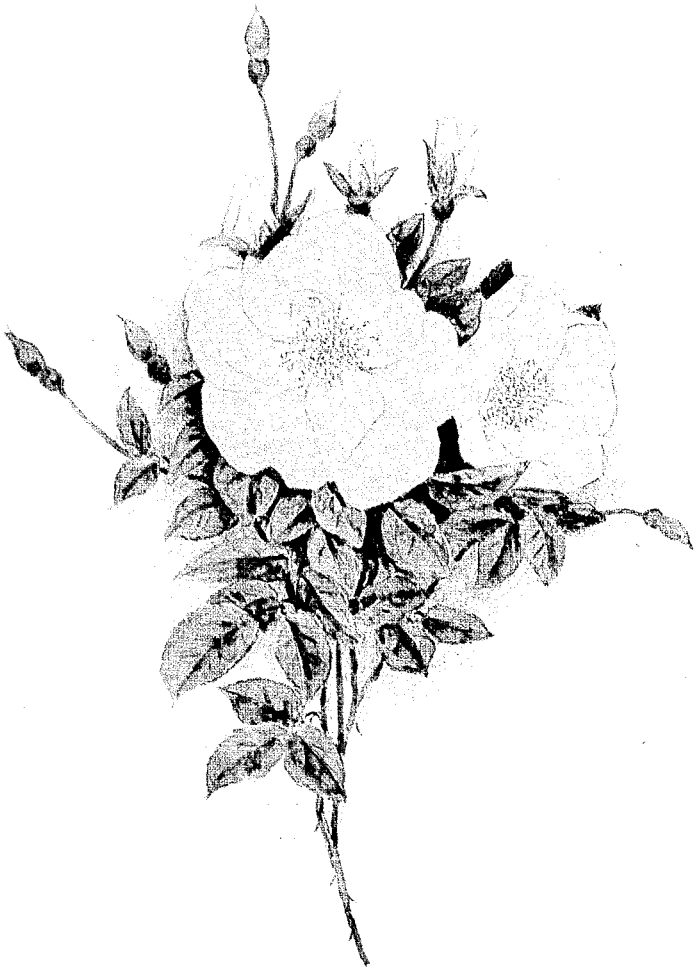
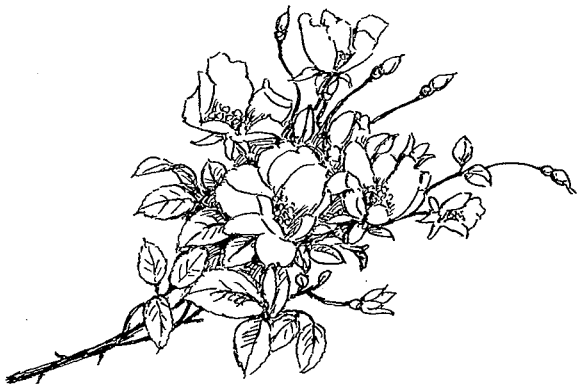
WITNESS
Addison E. Avery
INVENTOR
Edward Burton Le Grice,
by: John H. Leonard,
his ATTY.

United States Patent Office

Plant Pat. 2,189
Patented Nov. 6, 1962

2,189
ROSA FLORIBUNDA PLANT

Edward Burton Le Grice, North Walsham, Norfolk, England

Filed May 2, 1961, Ser. No. 107,276
1 Claim. (Cl. 47—61)

This invention relates to a new variety of Rosa Floribunda plant.

The present rose plant was produced originally by the crossing of an unnamed seedling as a seed parent and an unnamed seedling as the pollen parent.

The parentage goes back to a generation raised before World War II. Rosa Californica and Lavender Pinocchio, Plant Patent No. 947, were introduced into the stream the third and second generations back.

The new variety was developed intentionally by me in my hybridizing greenhouse in North Walsham, England in 1956.

The new variety was asexually reproduced by me in 1957, at North Walsham, England, by budding. The new variety has been tested there and, in 1958, at Mentor, Ohio, and in 1959 by the National Rose Society, St. Albans, England.

The drawing shows in color a number of typical stalks with leaves, buds, blooms and thorns, and in an ink sketch the general manner of growth.

The exposed portion of the plant is in the form of a woody, hardy penennial bush, upright and symmetrical in shape, and flattened on top. It is dense and compact and grows generally to a height of about 2 to 2½ feet and has a spread of about 2 feet at three years. It is a short, but vigorous, grower.

The exposed portion of the plant has good resistance to low temperatures when protected and fair resistance when unprotected. The resistance of this variety to drought and to wet seasons is good.

For growth, it prefers moderate sun and partial shade with a south and west exposure. It thrives in a rich, well drained, loam soil.

The main stalks of the plant are upright, slightly branched and stiff. They are adequate to support the foliage and blooms well.

The following color designations are from the British Color Council Horticultural Color Chart and are designated by sheet and number.

The new growth of the stalks is Erythrite Red, ranging from Sheet 190, No. 0027/1 to No. 0027/3. The old growth ranges from Willow Green, Sheet 199, No. 000862 to Spinach Green, Sheet 187, No. 0960/3. The color is uniform on the old and on the new growth.

The main stalks range from about 9 inches to 15 inches in length and are curving and divergent. They have a prickly surface texteure. The branches are alternate and prickly, many in quantity and tough. They are adequate to support the foliage and blooms.

The foliage in general is dense. The leaf arrangement is alternate and whorled. The leaves are abundant in quantity. The new leaves, on the top and bottom surfaces, are Willow Green, Sheet 199, No. 000862.

The old leaves, on the top and bottom surfaces, are a uniform Willow Green, Sheet 199, No. 000862. The new leaves are variegated and heavily overlaid with Erythrite Red, Sheet 190, No. 0027 to No. 0027/1.

The leaves are of average size, ranging from 2½ inches to 5 inches in length and in width from two inches to 4½ inches. They are of the usual shape, being imparipinnate with serrated margins, sagittate bases, and acute apices. They are of average thickness. They are smooth on the upper face and dull on the reverse. Their persistency on the plant is excellent and their characteristics are normal.

The petioles or leaf stems are Willow Green, Sheet 199, No. 000862. They are average in length, being about 1 inch, and are medium in strength. They have a glossy surface texture.

The stipules are short, being about 1½ inches and small.

The plant grows and blooms well in temperate regions. It prefers sun and an eastern, southern, or western exposure, wet, cold seasons, and a well drained, rich loam soil which is approximately neutral or of about pH 6.5 Changes in exposure, wetness, coldness of season and quality of soil do not cause much variation in the quality of the blooms. The blooms open well in all weather. Their quantity increases under optimum conditions. The blossom color is Pastel Mauve, Sheet 127, No. 433. The blooming improves under ideal conditions and the color of the blooms remains fairly stable.

The blooming is continuous for a period of about five months. The blooming characteristics are not changed appreciably by cutting the blooms in the bud stage. The cut buds open well in water. The uncut flowers drop cleanly at the end of the blooming period.

The buds are medium in size and elongated in shape. Their aspect is glossy. They are supported upright in clusters on terminals and laterals. Their pedicels are strong.

When the sepals first divide, the petal color is Venetian Pink, Sheet 125, No. 420. When the petals begin to unfurl, the color is Venetian Pink, Sheet 125, No. 420. When half blown, the color is Pastel Mauve, Sheet 127, No. 433.

Their pedicels are strong. The buds open rapidly. Heat hastens their opening.

The sepals are of the usual shape and size.

The calyx is of usual shape and size with a smooth surface texture.

The peduncles average from 2 inches to 12 inches in length, according to cluster or single flower. They have stipules at the flower stalk axes. Their color generally varies from Willow Green, Sheet 199, No. 000862/1 to the same but shaded Erythrite Red, Sheet 190, No. 0027/2. They are medium in strength.

The pedicles average from 2 inches to 2½ inches in length. Their texture is rough with tiny bristles and the color generally is Willow Green, Sheet 199, No. 000862 with bristles of Erythrite Red, Sheet 190, No. 0027.

The blooms average from 2 inches in diameter to 3 inches and an average plant will bear from 50 to 60 flowers at the same time. The blooms are borne in racemes. Each flower lasts from 2 to 3 days, both cut and uncut.

Each bloom has 5 to 8 petals colored Pastel Mauve, Sheet 127, No. 433. The coloring of each petal is uniform, both inside and reverse, from the center of the flower to the outer edges, except for a very small zone of Aureolin Yellow, Sheet 3, No. 3/3 at the base of each petal.

The general tonality of the plant from a distance, when it is in bloom, is Pastel Mauve, paling slightly with age.

The petals are waxy on the inside and outside and are relatively smooth and flat. The arrangement of the petals is usual. There are from 1 to 4 petaloids and their persistence is good both on the cut and uncut bloom. The bloom is a rounded single rose.

The fragrance of the blooms is a medium brier quality perfume and its lasting quality is good for cut blooms and persistent for uncut blooms.

The stamens are normal in size, shape, and quantity. Their filaments are long incurved and, in color, ranging from Crimson No. 22 to Rose Red, Sheet 158, No. 724. The anthers are Saffron Yellow, Sheet 7, No. 7/1. The pollen is Saffron Yellow, Sheet 7, No. 7/2.

The styles are about ¼ of an inch in length and Saffron Yellow, Sheet No. 7/3. The stigmas are about 1/16 of an inch and are colored Venetian Pink, Sheet 125, No. 420/3. The ovaries are medium.

There are thorns on the main stalk from the base of the plant and on the laterals from the stalks. They are moderate in quantity, long, and wedge shaped. Their color is Rhodonite Red, Sheet 188, No. 0022. They are evenly distributed on the main stalk and on the laterals and are absent from the peduncles.

The drawing further illustrates the characteristics of the variety and the following tabulation is a detailed description of the new variety:

*General*

Parentage:
- *Seed parent.*—Unnamed seedling.
- *Pollen parent.*—Unnamed seedling.
- Rosa Californica and Lavender Pinocchio introduced into stream during third and second generations back.

Classification: Botanic—Rosa Floribunda.

Blooming habit:
- *Location where observations were made.*—North Walsham, England; National Rose Society Trial Grounds, St. Albans, England; Mentor, Ohio, U.S.A.
- *Flowering.*—Continuous for about five months.

Bud:
- *Size.*—Medium.
- *Form.*—Elongated.
- *Color.*—When sepals first divide, the petals are Venetian Pink, Sheet 125, No. 420. When petals begin to unfurl, they are also Venetian Pink, Sheet 125, No. 420. When half blown, they are Pastel Mauve, Sheet 127, No. 433.
- *Sepals.*—Of the usual shape and size.
- *Calyx.*—Of the usual shape and size with a smooth surface texture.
- *Peduncle.*—Length—from 2 to 12 inches according to cluster or single flower. Aspect—stipules at the flower stalk axes. Color—varying from Willow Green, Sheet 199, No. 000862/1 shaded Erythrite Red, Sheet 190, No. 0027/2.
- *Pedicels.*—Length—from 2 to 2½ inches. Texture—rough with tiny bristles. Color—Willow Green, Sheet 199, No. 000862 with bristles of Erythrite Red, Sheet 190, No. 0027. They are strong.
- *Opening.*—Rapid after bud stage, increased with temperature.

Bloom:
- *Size.*—2 to 3 inches in diameter. Average bloom per plant—50 to 60.
- *Borne.*—In racemes.
- *Stems.*—Length—about 1 inch; medium. Aspect—glossy. Color—Willow Green, Sheet 199, No. 000862.
- *Form.*—Rounded single rose.
- *Permanence.*—2 to 3 days, both cut and uncut.

Petalage:
- *Number of petals under normal conditions.*—5 to 8.
- *Color.*—Pastel Mauve, Sheet 127, No. 433, with a very small zone of Aureolin Yellow, Sheet 3, No. 3/3 at the base of each petal.
- *Variegations.*—As per above. Reverse of petals—Pastel Mauve, Sheet 127, No. 433.
- *Discoloration.*—Paling slightly with age.

Petals:
- *Texture.*—Waxy.

- *Appearance.*—Waxy on the inside and outside.
- *Form.*—Smooth and flat.
- *Arrangement.*—Usual for single type.
- *Petaloids.*—1 to 4 in center of bloom.
- *Persistence.*—Good both cut and uncut.
- *Fragrance.*—Medium sweet brier perfume.
- *Lasting quality.*—Good for cut blooms and persistent for uncut blooms.

Genital organs:
- *Stamens.*—Normal in size, shape and quantity. Color—Saffron Yellow, Sheet 7, No. 7/1.
- *Filaments.*—Long incurved, color—ranging from Crimson No. 22 to Rose Red, Sheet 158, No. 724.
- *Pollen.*—Saffron Yellow, Sheet 7, No. 7/2.
- *Styles.*—¼ inch, color—Saffron Yellow, Sheet 7, No. 7/3.
- *Stigmas.*—About 1/16 inch, color—Venetian Pink, Sheet 125, No. 420/3.
- *Ovaries.*—Medium.

*Plant*

Form: A hardy woody bush, upright and dense, with a flat top.

Growth: Short but vigorous. Height from 2 to 2½ feet high and 2 feet wide at 3 years.

Foliage: Dense; leaves alternate, abundant in quantity.
- *Size.*—Average length from 2½ to 5 inches, and width from 2 to 4½ inches.
- *Quantity.*—Abundant.
- *Color.*—New leaves Willow Green, Sheet 199, No. 000862 on top and bottom, heavily overlaid with Erythrite Red, Sheet 190, Nos. 0027/1 to 0027. Old leaves on top and bottom are Willow Green, Sheet 199, No. 000862 and uniform.
- *Shape.*—Imparipinnate with serrated margins, sagittate bases and acute apices.
- *Texture.*—Upper face—smooth. Lower face—dull. Average thickness.
- *Edge.*—Serrated Willow Green, Sheet 199, No. 000862.

Petiole: Length, about 1 inch with glossy surface texture. Medium strength and Willow Green, Sheet 199, No. 000862 in color.

Stipules: Short—1½ inches and small. Color—Willow Green, Sheet 199, No. 000862.

Wood:
- *Newest wood.*—Color—Erythrite Red, Sheet 190, No. 0027/3.
- *Bark.*—Prickly.
- *Old wood.*—Willow Green, Sheet 199, No. 000862 to Spinach Green, Sheet 187, No. 0960/3 and prickly.

Thorns:
- *Quantity.*—Moderate on main stalks and on laterals.
- *Form.*—Long and wedge shaped.
- *Color.*—Rhodonite Red, Sheet 188, No. 0022.
- *Position.*—Evenly distributed on main stalks and on the laterals and absent from the peduncles.

This rose is characterized by its mauve coloring, similar to a mauve clematis, and by its golden center, entwined by the red filaments of the anthers. There is no known rose of this color or combining these features. It is suitable both for decoration and for bedding.

Having shown and described my new variety of Rosa Floribunda plant and its manner of asexual reproduction, I claim:

The new and distinct variety of Rosa Floribunda plant herein shown and described.

No references cited.